(12) United States Patent
Gravekamp

(10) Patent No.: US 11,213,577 B2
(45) Date of Patent: Jan. 4, 2022

(54) TREATMENT OF CANCER USING RECALL ANTIGENS DELIVERED BY ATTENUATED BACTERIA

(71) Applicant: ALBERT EINSTEIN COLLEGE OF MEDICINE, INC., Bronx, NY (US)

(72) Inventor: Claudia Gravekamp, New York, NY (US)

(73) Assignee: Albert Einstein College of Medicine, Inc., Bronx, NY (US)

( * ) Notice: Subject to any disclaimer, the term of this patent is extended or adjusted under 35 U.S.C. 154(b) by 0 days.

(21) Appl. No.: 15/568,491

(22) PCT Filed: Apr. 26, 2016

(86) PCT No.: PCT/US2016/029283
§ 371 (c)(1),
(2) Date: Oct. 23, 2017

(87) PCT Pub. No.: WO2016/176164
PCT Pub. Date: Nov. 3, 2016

(65) Prior Publication Data
US 2018/0104320 A1   Apr. 19, 2018

Related U.S. Application Data

(60) Provisional application No. 62/153,728, filed on Apr. 28, 2015.

(51) Int. Cl.
| | | |
|---|---|---|
| *A61K 39/02* | (2006.01) | |
| *A61K 39/00* | (2006.01) | |
| *A61K 35/74* | (2015.01) | |
| *C07K 14/33* | (2006.01) | |
| *C07K 14/005* | (2006.01) | |
| *A61K 39/08* | (2006.01) | |
| *A61P 35/04* | (2006.01) | |
| *A61K 39/39* | (2006.01) | |
| *A61K 45/00* | (2006.01) | |
| *C07K 14/105* | (2006.01) | |
| *C07K 14/12* | (2006.01) | |
| *C12N 1/36* | (2006.01) | |

(52) U.S. Cl.
CPC .......... *A61K 39/0011* (2013.01); *A61K 35/74* (2013.01); *A61K 39/08* (2013.01); *A61K 39/39* (2013.01); *A61K 45/05* (2013.01); *A61P 35/04* (2018.01); *C07K 14/005* (2013.01); *C07K 14/105* (2013.01); *C07K 14/12* (2013.01); *C07K 14/33* (2013.01); *C12N 1/36* (2013.01); *A61K 2039/5154* (2013.01); *A61K 2039/522* (2013.01); *A61K 2039/585* (2013.01); *C12N 2760/18422* (2013.01); *C12N 2760/18433* (2013.01); *C12N 2770/32622* (2013.01); *C12N 2770/32633* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 6,312,700 B1 | 11/2001 | Weinberg | |
| 7,820,180 B2 | 10/2010 | Singh et al. | |
| 8,669,091 B2* | 3/2014 | Gentschev | A61P 5/14 435/252.3 |
| 2006/0263389 A1 | 11/2006 | Stacy et al. | |
| 2011/0287037 A1* | 11/2011 | Gentschev | A61K 39/00 424/184.1 |

FOREIGN PATENT DOCUMENTS

WO     2005005465 A2     1/2005

OTHER PUBLICATIONS

Bachman et al (Journal of Immunology, 2005, vol. 175, pp. 4677-4685) (Year: 2005).*
Efferson et al (Anticancer research, 2005, vol. 25, pp. 715-724) (Year: 2005).*
Gravekamp et al. Journal of Geriatric S33-S102, 2012, (Year: 2012).*
Chandra et al. BJC , vol. 108, pp. 2281-2290, 2013. (Year: 2013).*
Communication Supplementary European Search Report dated Oct. 30, 2018 in connection with European Patent Application No. 16786975.9.
Kim S H et al., entitled "High Efficacy of a Listeria-Based Vaccine against Metastatic Breast Cancer Reveals a Dual Mode of Action," Cancer Research, vol. 69, No. 14, Jul. 15, 2009, pp. 5860-5866.
Quispe-Tintaya W et al., entitled "Nontoxic radioactive Listeriaat is a highly effective therapy against metastatic pancreatic cancer," PNAS, vol. 110, No. 21, Apr. 22, 2013, pp. 8668-8673.
Chandra D et al., entitled "Abstract B076: Novel use of Listeria and gemcitabine to improve immunotherapy for pancreatic cancer," Cancer Immunol Res, vol. 4, No. 1 Suppl, Sep. 16, 2015, 5 pages.
Gravekamp, C et al., entitled "Harnessing Listeria monocytogenes to target tumors," Cancer Biology & Therapy, vol. 9, No. 4, Feb. 15, 2010, pp. 257-265.
Jahangir A et al., entitled Immunotherapy with Listeria reduces metastatic breast cancer in young and old mice through different mechanisms, Oncomimmunology, vol. 6, No. 9, Jul. 5, 2017, e1342025 (15 pages).
PCT International Search Report and Written Opinion dated Aug. 26, 2016 for PCT International Patent Application No. PCT/US2016/29283, 11 pages.

* cited by examiner

*Primary Examiner* — Jana A Hines
*Assistant Examiner* — Khatol S Shahnan Shah
(74) *Attorney, Agent, or Firm* — Timothy J. Bortree

(57) ABSTRACT

Methods, pharmaceutical compositions and vaccines comprising an attenuated bacteria that expresses a recall antigen are disclosed for treatment of cancer.

5 Claims, 9 Drawing Sheets
Specification includes a Sequence Listing.

TREATMENT OF CANCER USING RECALL ANTIGENS DELIVERED BY ATTENUATED BACTERIA

CROSS-REFERENCE TO RELATED APPLICATIONS

This application is a U.S. national stage entry under 35 U.S.C. § 371 of PCT International Patent Application No. PCT/US2016/029283, filed Apr. 26, 2016, which claims the benefit of U.S. Provisional Patent Application No. 62/153,728, filed Apr. 28, 2015, the contents of each of which are incorporated herein by reference into the subject application.

BACKGROUND OF THE INVENTION

Throughout this application various publications are referred to in parentheses or superscript. Full citations for these references may be found at the end of the specification. The disclosures of these publications are hereby incorporated by reference in their entirety into the subject application to more fully describe the art to which the subject invention pertains.

Cancer remains a major health concern in the U.S. and abroad. In 2011, there were an estimated 13,397,159 people living with cancer in the United States. Based on age-adjusted data from 2007-2011, the number of new cases of cancer per year was 460.4 per 100,000 men and women. The number of deaths per year was 173.8 per 100,000 men and women. Approximately 40.4 percent of men and women are expected to be diagnosed with cancer at some point during their lifetime, based on 2009-2011 data. It is expected that annual cancer cases will rise from 14 million in 2012 to 22 million within the next 2 decades (World Cancer Report 2014).

Success of cancer immunotherapy is hindered by two major problems. One problem is that tumor-associated antigens (TAA), used in cancer vaccines, are often self-antigens that are overexpressed or mutated in tumor cells compared to normal cells. The T cells in the thymus have been taught earlier in life not to react to self-antigens, and therefore it is difficult to induce strong T cell responses to TAA. The other problem is that most cancer patients are old, and the elderly react less efficiently to vaccines than young adults. This is often due to lack of naïve T cells (only generated at young age, and are used during life) that react for the first time to a new antigen and are responsible for the generation of memory T cells upon repeated exposures with the same antigen. The present invention addresses both of these problems and the need for improved treatments for cancers and in particular for improved treatments for metastases.

SUMMARY OF THE INVENTION

The present invention provides methods of treating tumors in a subject, and/or reducing or preventing metastasis of tumors in a subject, comprising administering to the subject an attenuated bacteria that expresses a recall antigen in an amount effective to treat the tumor, and/or to reduce or prevent metastasis of the tumor.

Also provided are pharmaceutical compositions and cancer vaccines comprising an attenuated bacteria that expresses a recall antigen.

DETAILED DESCRIPTION OF THE INVENTION

Figure 1:
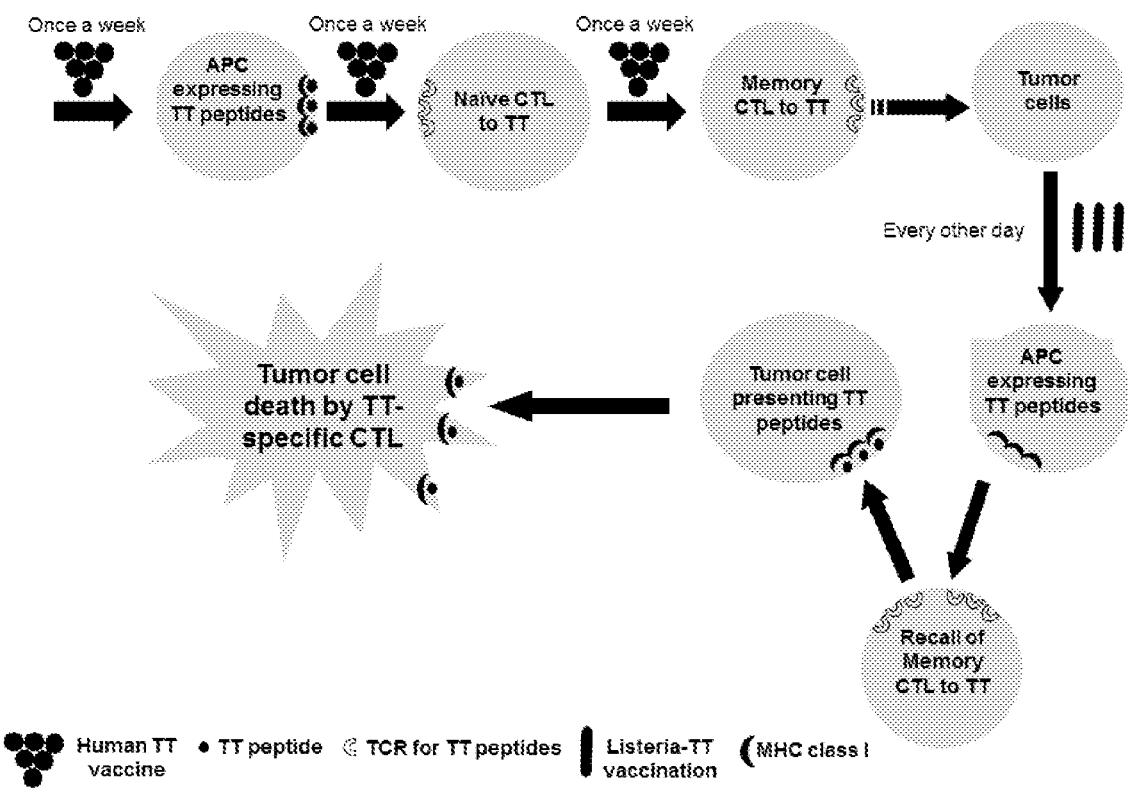
FIG. 1. Schematic view of the *Listeria*-recall antigen model.

The present invention provides a method of treating a tumor in a subject, and/or reducing the incidence or likelihood of metastasis of a tumor in a subject, comprising administering to the subject an attenuated bacteria that expresses a recall antigen in an amount effective to treat the tumor, and/or to reduce the incidence or likelihood of metastasis of the tumor.

The bacteria can be, for example, one of more of *Listeria monocytogenes, Salmonella thyphimurium, Vibrio cholera, Clostridium*, and *Bifidobacterium breve*. In a preferred embodiment, the bacteria are *Listeria monocytogenes*. The bacteria are attenuated to reduce or eliminate virulence. As used here, attenuated *Listeria*, for example, is denoted as *Listeria$^{at}$*.

As used herein, a recall antigen is an antigen to which a subject has previously been exposed earlier in life. Recall antigens can include, for example, antigens used for childhood vaccinations, such as tetanus toxoid, measle virus, and poliovirus antigens. Most individuals have been vaccinated and boosted with these antigens during childhood, resulting in memory T cells that circulate in their blood stream for life. These memory T cells can be reactivated at any age, even in a tumor microenvironment.

Examples of recall antigens that can be used include, but are not limited to, an epitope or an fragment containing one or more immunodominant epitopes of one or more of tetanus toxoid, measle virus, and polio virus. In a preferred embodiment, the antigen is a tetanus toxoid fragment containing one or more immunodominant epitopes.

This principle is not only applicable to childhood antigens, but to almost any immunogenic antigen that patients have seen earlier in life. For example, up to 70% of all women acquire a *Candida albicans* infection earlier or later in life (1), which expresses highly immunogenic proteins including heat-shock protein (Hsp)70(2). On the other hand, flu virus is less suitable because of their continuous antigenic drift. Basically, the number of immunogenic antigens to be used for this approach is unlimited.

As an example, shown below are the Tetanus toxoid (TT) (aa position 856-1313) amino acid (upper case) (SEQ ID NO:5) and DNA (lower case) (SEQ ID NO:6) sequence cloned into *Listeria* (see Experimental Details). The underlined and bold portions of the DNA sequence represent primer sequences used for cloning TT into *Listeria*. The underlined and bold portions of the amino acid sequence represent CD8 epitopes in TT immunodominant in the Panc-02 model (C57B16 mice). The portion of the amino acid sequence in italics and bold font represents the CD8 epitope in TT immunodominant in the 4T1 model (BALB/c mice).

```
5'
tcaacaccaattccatttctcttattctaaaaatctggattgttgggttgataatgaagaa
 S  T  P  I  P  F  S  Y  S  K  N  L  D  C  W  V  D  N  E  E gatatagatgttatattaaaaaagagtacaattttaaatttagatattaataatgatatt
 D  I  D  V  I  L  K  K  S  T  I  L  N  L  D  I  N  N  D  I atatcagatatatctgggtttaattcatctgtaataacatatccagatgctcaattggtg
 I  S  D  I  S  G  F  N  S  S  V  I  T  Y  P  D  A  Q  L  V cccggaataaatggcaaagcaatacatttagtaaacaatgaatcttctgaagttatagtg
 P  G  I  N  G  K  A  I  H  L  V  N  N  E  S  S  E  V  I  V cataaagctatggatattgaatataatgatatgtttaataattttaccgttagcttttgg
 H  K  A  M  D  I  E  Y  N  D  M  F  N  N  F  T  V  S  F  W ttgagggttcctaaagtatctgctagtcatttagaacaatatggcacaaatgagtattca
 L  R  V  P  K  V  S  A  S  H  L  E  Q  Y  G  T  N  E  Y  S ataattagctctatgaaaaaacatagtctatcaataggatctggttggagtgtatcactt
 I  I  S  S  M  K  K  H  S  L  S  I  G  S  G  W  S  V  S  L
```

-continued

```
aaaggtaataacttaatatggactttaaaagattccgcgggagaagttagacaaataact
 K  G  N  N  L  I  W  T  L  K  D  S  A  G  E  V  R  Q  I  T tttagggatttacctgataaatttaatgcttatttagcaaataaatgggttttttataact
 F  R  D  L  P  D  K  F  N  A  Y  L  A  N  K  W  V  F  I  T attactaatgatagattatcttctgctaatttgtatataaatggagtacttatgggaagt
 I  T  N  D  R  L  S  S  A  N  L  Y  I  N  G  V  L  M  G  S gcagaaattactggtttaggagctattagagaggataataatataacattaaaactagat
 A  E  I  T  G  L  G  A  I  R  E  D  N  N  I  T  L  K  L  D agatgtaataataataatcaatacgtttctattgataaatttaggatattttgcaaagca
 R  C  N  N  N  Q  Y  V  S  I  D  K  F  R  I  F  C  K  A ttaaatccaaaagagattgaaaaattatacacaagttatttatctataacctttttaaga
 L  N  P  K  E  I  E  K  L  Y  T  S  Y  L  S  I  T  F  L  R gacttctggggaaaccctttacgatatgatacagaatattatttaataccagtagcttct
 D  F  W  G  N  P  L  R  Y  D  T  E  Y  Y  L  I  P  V  A  S agttctaaagatgttcaattgaaaaatataacagattatatgtatttgacaaatgcgcca
 S  S  K  D  V  Q  L  K  N  I  T  D  Y  M  Y  L  T  N  A  P tcgtatactaacggaaaattgaatatatattatagaaggttatataatggactaaaattt
 S  Y  T  N  G  K  L  N  I  Y  Y  R  R  L  Y  N  G  L  K  F attataaaaagatatacacctaataatgaaatagattcttttgttaaatcaggtgatttt
 I  I  K  R  Y  T  P  M  M  E  I  D  S  F  V  K  S  G  D  F attaaattatatgtatcatataacaataatgagcacattgtaggttatccgaaagatgga
 I  K  L  Y  V  S  Y  N  N  N  E  H  I  V  G  Y  P  K  D  G aatgcctttaataatcttgatagaattctaagagtaggttataatgccccaggtatccct
 N  A  F  N  N  L  D  R  I  L  R  V ctttataaaaaaatggaagcagtaaaattgcgtgatttaaaaacctattctgtacaactt
 L  Y  K  K  M  E  A  V  K  L  R  D  L  K  T  Y  S  V  Q  L aaattatatgatgataaaaatgcatctttaggactagtaggtacccataatggtcaaata
 K  L  Y  D  D  K  N  A  S  L  G  L  V  G  T  H  N  G  Q  I ggcaacgatccaaatagggatatattaattgcaagcaactggtacttaatcatttaaaa
 G  N  D  P  N  R  D  I  L  I  A  S  N  W  Y  F  N  H  L  K gataaaattttaggatgtgattggtactttgtacctacagatgaaggatggaca 3'
 D  K  I  L  G  C  D  W  Y  F  V  P  T  D  E  G  W  T.
```

Also as an example, shown below are the poliovirus (PV) (aa position: 49-273 in VP1) amino acid (SEQ ID NO:7) and DNA (SEQ ID NO:8) sequence cloned into *Listeria*. The underlined and bold portions of the DNA sequence represent primer sequences used for cloning PV VP1 into *Listeria*. The portions of the amino acid sequence in italics and bold font represent CD8 epitopes in PV VP1 immunodominant in the 4T1 model (BALB/c mice/H2-d haplotype).

```
5'
aggtcaaggtcagagtctagcatagagtctttcttcgcgcggggtgcatgcgtg
                       R  S  R  S  E  S  S  I  E  S  F  F  A  R  G  A  C  V accattatgaccgtggataacccagcttccaccacgaataaggataagctatttgcagtg
 T  I  M  T  V  D  N  P  A  S  T  T  N  K  D  K  L  F  A  V tggaagatcacttataaagatactgtccagttacggaggaaattggagttcttcacctat
 W  K  *I  T  Y  K  D  T  V  Q  L  R  R*  K  L  E  F  F  T  Y tctagatttgatatggaacttacctttgtggttactgcaaatttcactgagactaacaat
 S  R  F  D  M  E  L  T  F  V  V  T  A  N  F  T  E  T  N  N gggcatgccttaaatcaagtgtaccaaattatgtacgtaccaccaggcgctccagtgccc
 G  H  A  L  N  Q  V  Y  Q  I  M  Y  V  P  P  G  A  P  V  P gagaaatgggacgactacacatggcaaacctcatcaaatccatcaatcttttacacctac
 E  K  W  D  D  Y  T  W  Q  T  S  S  N  P  S  I  F  Y  T  Y ggaacagctccagcccggatctcggtaccgtatgttggtatttcgaacgccattcacac
 G  T  A  P  A  R  I  S  V  P  Y  V  G  I  *S  N  A  Y  S  H* ttttacgacggttttttccaaagtaccactgaaggaccagtcggcagcactaggtgactcc
 *F  Y  D  G  F  S  K  V  P  L  K  D  Q  S*  A  A  L  G  D  S
```

-continued
```
ctttatggtgcagcatctctaaatgacttcggtattttggctgttagagtagtcaatgat
 L   Y   G   A   A   S   L   N   D   F   G   I   L   A   V   R   V   V   N   D cacaacccgaccaaggtcacctccaaaatcagagtgtatctaaaacccaaacacatcaga
 H   N   P   T   K   V   S   K   I   I   R   V   Y   L   K   P   K   H   I   R gtctggtgcccgcgtccaccgagggcagtggcgtactacggccctggagtggattacaag
 V   W   C   P   R   P   P   R   A   V   A   Y   Y   G   P   G   V   D   Y   K gatggtacgcttacaccc 3'
 D   G   T   L   T   P.
```

As a further example, shown below are the measlevirus (MV) amino acids (Nucleocapsid aa position: 38-351) amino acid (SEQ ID NO:9) and DNA (SEQ ID NO:10) sequence cloned into *Listeria*. The underlined and bold portions of the DNA sequence represent primer sequences used for cloning of the MV sequence into *Listeria*. The portions of the amino acid sequence in italics and bold font represent CD8 epitopes in MV immunodominant in the 4T1 model (AKR mice/H2-k haplotype).

5' ccaatccctggagat
 P  I  P  G  D tcctcaattaccactcgatccagacttctggaccggttggtcaggttaattggaaacccg
 S  S  I  T  T  R  S  R  L  *L D R L V R L I G*  N  P gatgtgagcgggcccaaactaacaggggcactaataggtatattatccttatttgtggag
 D  V  S  G  P  K  L  T  G  A  L  I  G  I  L  S  L  F  *V E* tctccaggtcaattgattcagaggatcaccgatgaccctgacgttagcataaggctgtta
 *S P G Q L I*  Q  R  I  T  D  D  P  D  V  S  I  R  L  L gaggttgtccagagtgaccagtcacaatctggccttaccttcgcatcaagaggtaccaac
 E  V  V  Q  S  D  Q  S  Q  S  G  L  T  F  A  S  R  G  T  N atggaggatgaggcgaaccaatacttttcacatgatgatccaattagtagtgatcaatcc
 M  E  D  E  A  N  Q  Y  F  S  H  D  D  P  I  S  S  D  Q  S aggttcggatggttcgagaacaaggaaatctcagatattgaagtgcaagaccctgaggga
 R  F  G  W  F  E  N  K  E  I  S  D  I  E  V  Q  D  P  E  G ttcaacatgattctgggtaccatcctagcccaaatttgggccttgctcgcaaaggcggtt
 F  N  M  I  L  G  T  I  L  A  Q  I  W  A  L  L  A  K  A  V acggccccagacacggcagctgattcggagctaaga 3'
 T  A  P  D  T  A  A  D  S  E  L  R.

The tumor can be, for example, a tumor of one or more of the pancreas, ovary, uterus, neck, head, breast, prostate, liver, lung, kidney, neurones, glia, colon, testicle, or bladder. The tumor can be an inoperable tumor.

Preferably, prior to administration to the subject, the bacteria are cultured in yeast medium.

The method can further comprise administering Cytosine-phosphate-Guanine (CpG) to the subject as an adjuvant.

In one embodiment, prior to administration of bacteria to the subject, the subject is screened for their major histocompatibility complex (MHC) 1 haplotype and administered an antigen for which the subject shows a CD8 T cell recall response.

In one embodiment, prior to administration of bacteria to the subject, an epitope of the antigen is administered to the subject to generate memory T cells to the antigen. This method will be less effective in older subjects who have fewer naïve T cells than younger subjects.

Bacteria can be administered by different routes to the subject. For example, bacteria can be administered systemically to the subject, such as for example, by intravenous administration. Bacteria can be administered by direct injection to a tumor site in the subject. Myeloid-derived suppressor cells (MDSCs) can be used to deliver attenuated bacteria to the microenvironment of both primary and metastatic neoplastic lesions, where the attenuated bacteria spread from MDSCs into tumor cells (see, e.g., 10). The infected tumor cells then become a target for activated immune cells.

Preferably, the subject receives repeated administrations of attenuated bacteria that expresses the recall antigen. For example, the administration may be daily or every other day, for a period of several days until a satisfactory therapeutic outcome is achieved.

As used herein, "treating" a tumor means that one or more symptoms of the disease, such as the tumor itself, metastasis thereof, vascularization of the tumor, or other parameters by which the disease is characterized, are reduced, ameliorated, placed in a state of remission, or maintained in a state of remission. "Treating" a tumor also means that one or more hallmarks of the tumor may be eliminated or reduced by the treatment. Non-limiting examples of such hallmarks include uncontrolled degradation of the basement membrane and proximal extracellular matrix, migration, division, and organization of the endothelial cells into new functioning capillaries, and the persistence of such functioning capillaries. Preferably, the method is effective to reduce tumor growth and/or size.

As used herein, reducing or preventing metastasis of a tumor means that any of the symptoms of the disease, such as the metastases, the extent of spread thereof, the vascularization of the metastases or other parameters by which the disease is characterized are reduced, ameliorated, prevented, placed in a state of remission, maintained in a state of remission, or eliminated. Preferably, the method is effective to reduce metastases. The method can reduce the incidence or likelihood of metastasis of a tumor.

The method can further comprise administering to the subject a chemotherapeutic agent that reduces the number of myeloid-derived suppressor cells (MDSCs). Such chemotherapeutic agents include, for example, gemcitabine, Vitamin A derivates, Amiloride, CpG oligodeoxynucleotide (CpG ODN), Docetaxel, 5-Fluorouracil, GW2580, Sildenafi and Sinitinib (3, 4).

The subject can be a mammal. In different embodiments, the mammal is a mouse, rat, cat, dog, horse, donkey, mule, sheep, goat, cow, steer, bull, livestock, primate, monkey, or preferably a human. The human can be of different ages, such as for example, a person 60 years of age or older.

Also provided is a pharmaceutical composition comprising a pharmaceutically acceptable carrier and attenuated bacteria that expresses a recall antigen. The bacteria can be, for example, one of more of Listeria monocytogenes, Salmonella thyphimurium, Vibrio cholera, Clostridium, and Bifidobacterium breve. The recall antigen can be, for example, an epitope of one or more of tetanus toxoid, measle virus, and polio virus.

Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution. The pharmaceutically acceptable carrier used can depend on the route of administration. The pharmaceutical composition can be formulated for administration by any method known in the art, including but not limited to, oral administration, parenteral administration, intravenous administration, transdermal administration, intramuscular administration, intranasal administration, direct injection into a tumor site, and administration through an osmotic mini-pump.

Also provided is a cancer vaccine comprising attenuated bacteria that expresses a recall antigen. The bacteria can be, for example, one of more of Listeria monocytogenes, Salmonella thyphimurium, Vibrio cholera, Clostridium, and Bifidobacterium breve. The recall antigen can be, for example, an epitope of one or more of tetanus toxoid, measle virus, and polio virus.

This invention will be better understood from the Experimental Details, which follow. However, one skilled in the art will readily appreciate that the specific methods and results discussed are merely illustrative of the invention as described more fully in the claims that follow thereafter.

Experimental Details

Introduction

Listeria constructs were developed that express antigens with immunodominant epitopes of childhood recall antigens tetanus toxoid (TT), measle virus (MV), and poliovirus (PV). Repeated immunizations with Listeria-TT in mice with memory T cells to the TT nearly completely eliminates metastases in mice with metastatic breast cancer cancer without side effects. Listeria-TT combined with gemcitabine in mice with pancreatic cancer was even more effective that Listeria-TT alone, most likely because gemcitabine reduces immune suppression through the elimination of myeloid-derived suppressor cells (MDSCs).

Schematic View of the Listeria-Recall Antigen Model

FIG. 1 provides a schematic view of the Listeria-recall antigen model. Memory T cells to recall antigens such as TT can be generated with the human TT vaccine in BALB/cByJ mice. The TT proteins can be taken up by antigen-presenting cells (APC) and presented to naïve T cells. Upon repeated exposure, the naïve T cells will differentiate into memory T cells, which circulate in the blood stream for life. Subsequently, 4T1 tumor cells can be injected into the mammary fat pad (this can be done at young or old age), followed by frequent immunizations with low dose Listeria-TT once the tumor is palpable. This will recall the activation of the memory T cells to TT earlier in life. Simultaneously, TT will be delivered into the tumor cells through infection with Listeria-TT, resulting in the presentation of TT antigens. Finally, the TT-specific memory T cells will migrate to the tumor cells, and kill the 4T1 tumor cells now presenting TT epitopes.

Methods and Results

Figure 2A:
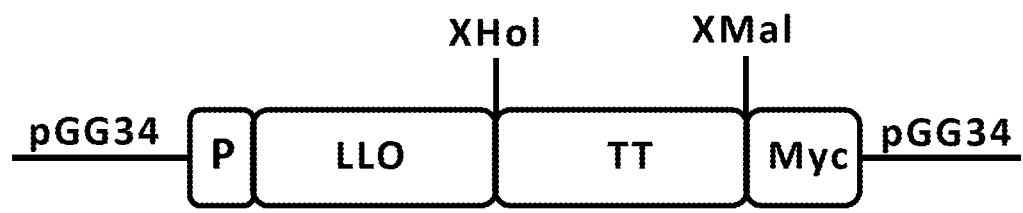
FIG. 2A. Development of the $Listeria^{at}$-$TT_{856-1313}$ vaccine. A non-toxic fragment of the C-terminus of tetanus toxoid (TT) cDNA (amino acid positions 856-1313) was cloned as a fusion protein with a truncated non-cytolytic ListeriolysinO (LLO) in the $Listeria^{at}$ plasmid pGG34, under the control of the LLO promoter (P)(A). A myc tag has been included for the detection of TT protein.
Figure 2B:
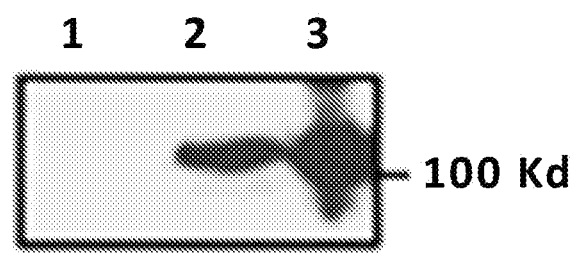
FIG. 2B Development of the $Listeria^{at}$-$TT_{856-1313}$ vaccine and testing TT expression of infected 4T1 tumor cells. Secretion of LLO-$TT_{856-1313}$ protein by LM-LLO-TT ($Listeria^{at}$-TT) was confirmed by western blotting using anti-myc antibodies. Lane 1: neg control (medium); Lane 2: supernatant of $Listeria^{at}$-TT culture; Lane 3: pellet of $Listeria^{at}$-TT culture.
Figure 2C:
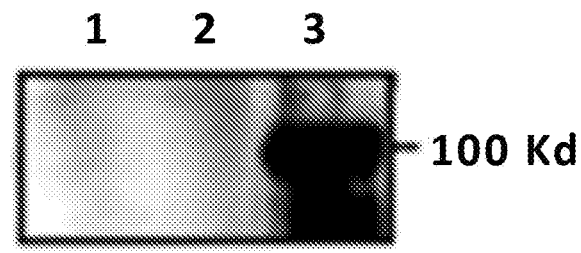
FIG. 2C. Development of the $Listeria^{at}$-$TT_{856-1313}$ vaccine and testing TT expression of infected 4T1 tumor cells. Infection with $Listeria^{at}$-TT resulted in the expression of TT antigens in the 4T1 tumor cells as shown here with anti-myc antibodies. Lane 1: 4T1 tumor cells; Lane 2: 4T1 tumor cells infected with $Listeria^{at}$; Lane 3: 4T1 tumor cells infected with $Listeria^{at}$-TT.

Development of the $Listeria^{at}$-$TT_{856-1313}$ vaccine. The Listeria-TT vaccine was developed as described below. The $TT_{856-1313}$ (62 kDa) was cloned as a fusion-protein with a truncated Listeriolysin O (LLO)(48 kDa) in the $Listeria^{at}$ vector (pGG34) under the control of the LLO promoter (P), and a myc sequence for detection of the TT protein (FIG. 2A). Secretion of LLO-$TT_{856-1313}$ protein by the $Listeria^{at}$-based vaccine was detected by western blotting using anti-myc antibodies (FIG. 2B). Infection of 4T1 tumor cells with $Listeria^{at}$-$TT_{856-1313}$ resulted in the expression of TT protein in the tumor cells (FIG. 2C). Also fragments of MV and PV have been cloned into the $Listeria^{at}$. Epitopes of the recall antigens that are immunodominant in mice are shown in Table 1.

Figure 3:
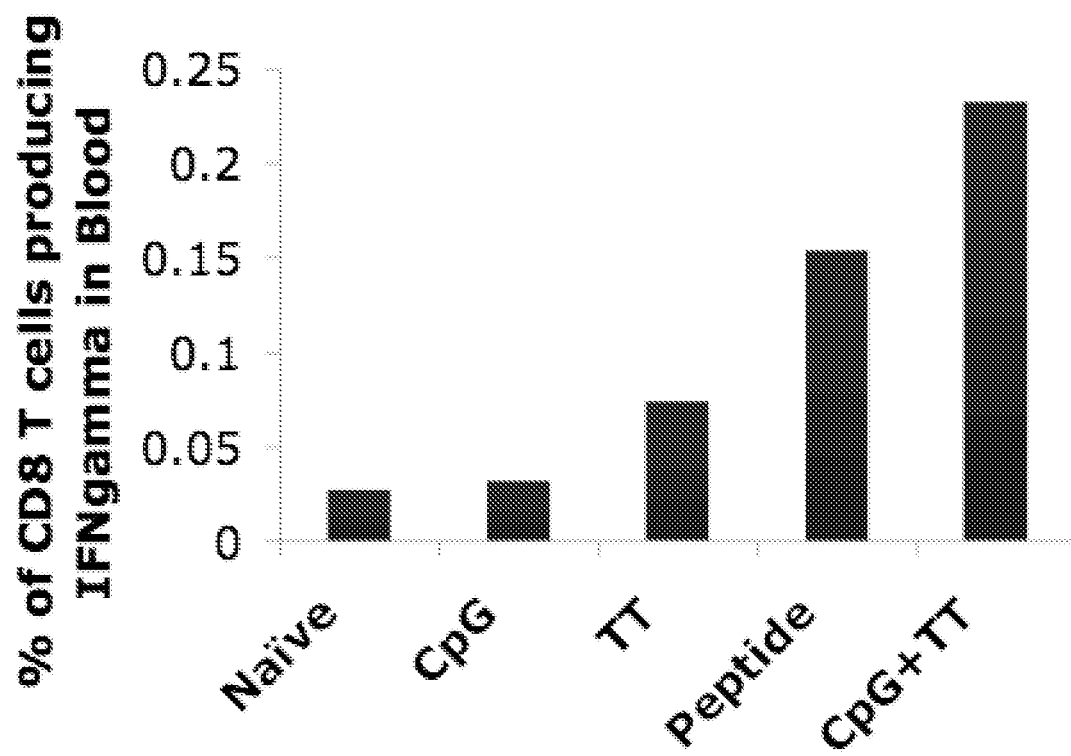
FIG. 3. Generation of CD8 T cell responses to immunodominant epitope within $TT_{856-1313}$ protein. BALB/cByJ mice received three immunizations with 5 µg of purified $TT_{856-1313}$ protein and 10 µg of CpG at 1-week time intervals, and white blood cells of treated and control mice were re-stimulated with the immunodominant CD8 TT peptide (GYNAPGIPL) (SEQ ID NO:1) for 72 h, and then they were analyzed by flow cytometry. Representative of 2 experiments. n=5 mice per group.

Generation of CD8 T cell responses to immunodominant epitope in $TT_{856-1313}$ protein. It was tested whether the $TT_{856-1313}$ protein induced CD8 T cell responses to the immunodominant epitope of $TT_{856-1313}$. For this purpose, BALB/cByJ mice were immunized three times with $TT_{856-1313}$ protein and CpG. Two days after the last immunization, mice were euthanized and white blood cells were restimulated with an immunodominant peptide GYNAPGIPL$_{1228-1236}$ (SEQ ID NO:1) within the $TT_{856-1313}$ protein (7). CD8 T cells were activated against the immunodominant $T_{1228-1236}$ epitope in blood of BALB/cByJ mice (FIG. 3).

Figure 4:
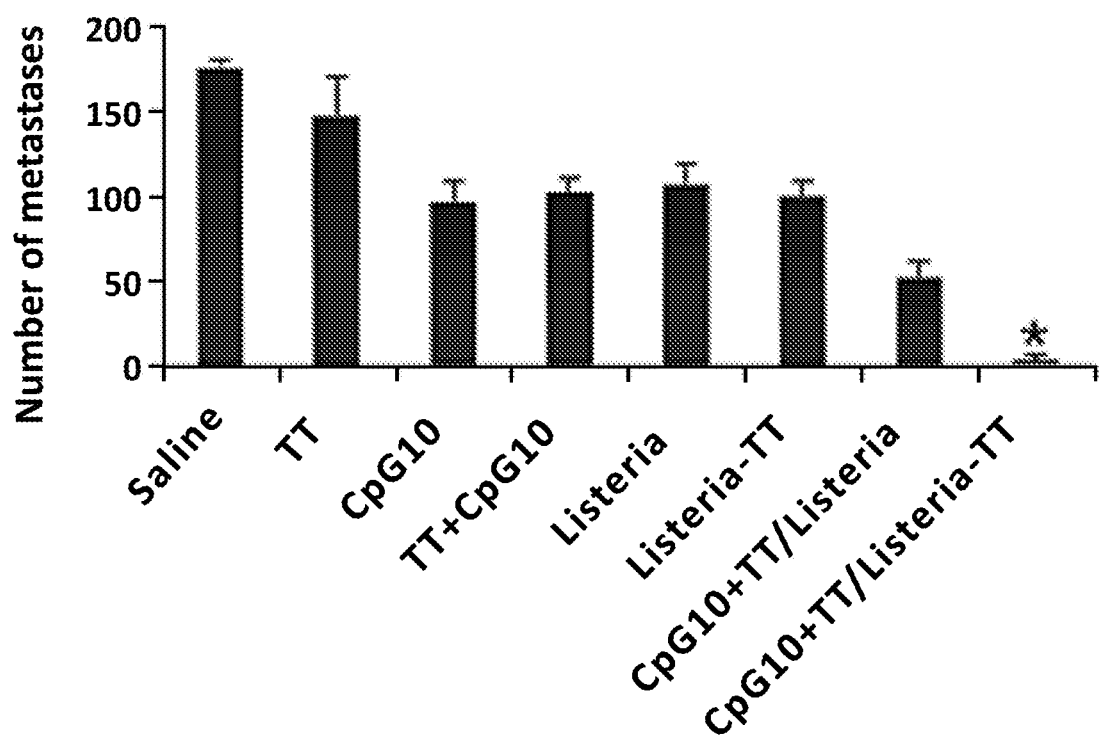
FIG. 4. $Listeria^{at}$-$TT_{856-1313}$ is highly effective against metastases in breast cancer model 4T1. BALB/cByJ mice were immunized with $TT_{856-1313}$ protein and CpG as described for FIG. 3. One week later, 4T1 tumor cells ($0.5 \times 10^5$) were injected into the mammary fat pad and immunizations with $Listeria^{at}$-TT were administered (every other day) after the tumor had reached 5 mm in diameter. This was continued for two weeks. Two days after the last immunization, all mice were euthanized and analyzed for the number of metastases. Average of two experiments with 5 mice per group. Mann-Withney test *p<0.05 is significant.

Vaccination with $Listeria^{at}$-$TT_{856-1313}$ is highly effective against metastases in breast cancer model 4T1. The efficacy of the Listeria-$TT_{856-1313}$ vaccine was tested against metastatic breast cancer in the 4T1 model. First, memory T cells to the immunodominant CD8 T cell epitope were generated with $TT_{856-1313}$ protein and CpG. Then, 4T1 tumor and metastases were generated by injection of the 4T1 cell line into the mammary fat pad, and $Listeria^{at}$-TT vaccinations were administered every other day for two weeks after the tumor size had reached 5 mm. $Listeria^{at}$-$TT_{856-1313}$ was highly effective against the metastases (FIG. 4) but not against the primary tumors (not shown). CpG was used as an adjuvant. Interestingly, CpG itself was also effective against the metastases. CpG was found to eliminate MDSC (3). $Listeria^{at}$ itself was also effective against metastases, by killing tumor cells through the production of ROS, in confirmation of earlier studies (12). However, the combination of CpG+TT/$Listeria^{at}$-$TT_{856-1313}$ was most effective, i.e. the number of metastases was significantly lower in the CpG+TT/$Listeria^{at}$-$TT_{856-1313}$ group compared to all control groups.

*Listeria*-TT and Gemcitabine is Highly Effective Against Metastases and Tumors in Mice with Pancreatic Cancer.

In clinical trials of *Listeria*-recall antigens in patients with pancreatic cancer, the patients would be expected to be treated with gemcitabine. Therefore, it was tested whether gemcitabine affected *Listeria*-recall antigen immunizations. Since gemcitabine is known for eliminating MDSCs, which are a major contributor to immune suppression, it was expected that gemcitabine will reduce immune suppression and the recall antigens can do their job better.

Figure 5:
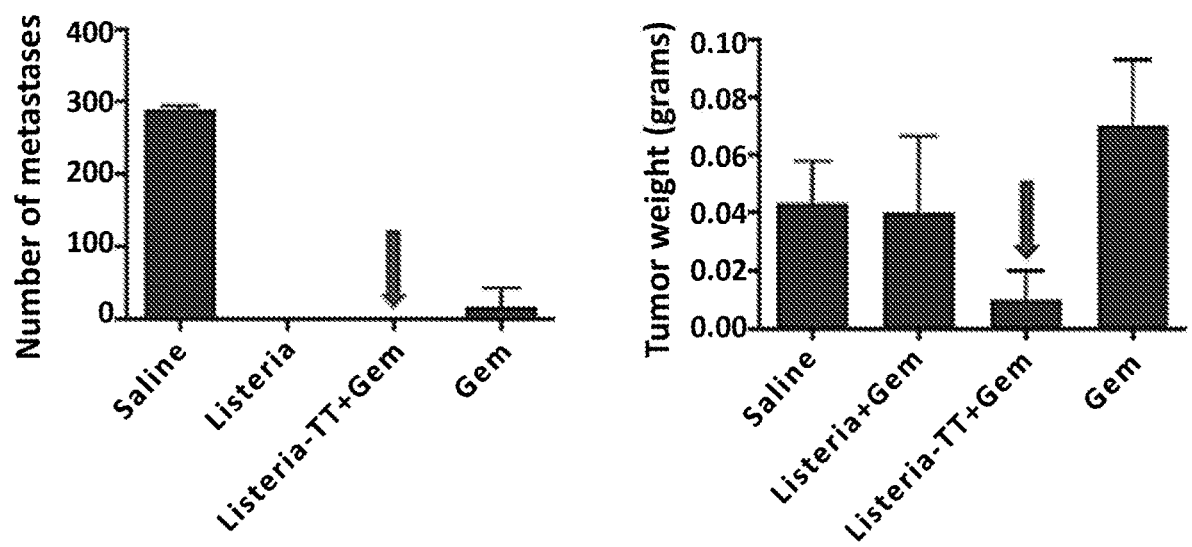
FIG. 5. Effect of *Listeria*-TT and gemcitabine (Gem) on metastases (left panel) and tumors (right panel) in a preclinical model pancreatic cancer (Panc-02). C57B16 mice were injected with $2 \times 10^6$ Panc-02 tumor cells in the mammary fat pad. Three days after tumor cell injection mice were treated with gemcitabine ip (1.2 mg/300 µl) every 3 days (6 treatments in total) throughout the whole study. $10^7$ CFU of *Listeria*-TT was injected every day ip, for 4 days, followed by a rest period of 3 days followed by 3 more injections with $10^7$ CFU of *Listeria*-TT every day. All mice were euthanized on day 21 and analyzed for the number of metastases and tumor weight. N=3 mice per group.

*Listeria* was starved in saline for 30 min, and subsequently cultured in yeast medium (keeps *Listeria* alive but *Listeria* does not replicate) for 60 min. This treatment allowed the injection of $10^7$ CFU of *Listeria* every day instead of $10^4$ CFU every day. Then, *Listeria*-TT was tested in combination with gemcitabine (Gem). Mice with pancreatic cancer were treated with gemcitabine ip (1.2 mg/300 μl per dose; every $3^{rd}$ day, starting day 3 after tumor cell injection), followed by *Listeria*-TT ip starting on day 10 after tumor cell injection ($10^7$ CFU every day for 4 days, followed by a rest period of 3 days, followed by another 3 injections with $10^7$ CFU of *Listeria*-TT). All mice were euthanized on day 21. Untreated mice will die between day 21-28 after tumor cell injection in this highly aggressive pancreatic cancer model. The combination of gemcitabine and *Listeria*-TT eliminated metastases completely and primary tumors nearly completely (FIG. 5). This was even much better than the *Listeria*-TT in the breast cancer model (4T1). The results suggest that gemcitabine improved the effect of TT on the Panc-02 tumor while the higher number of *Listeria* (10E7 instead of 10E4), completely eliminated the metastases. In conclusion, gemcitabine had a positive effect on *Listeria*-TT.

Figure 6:
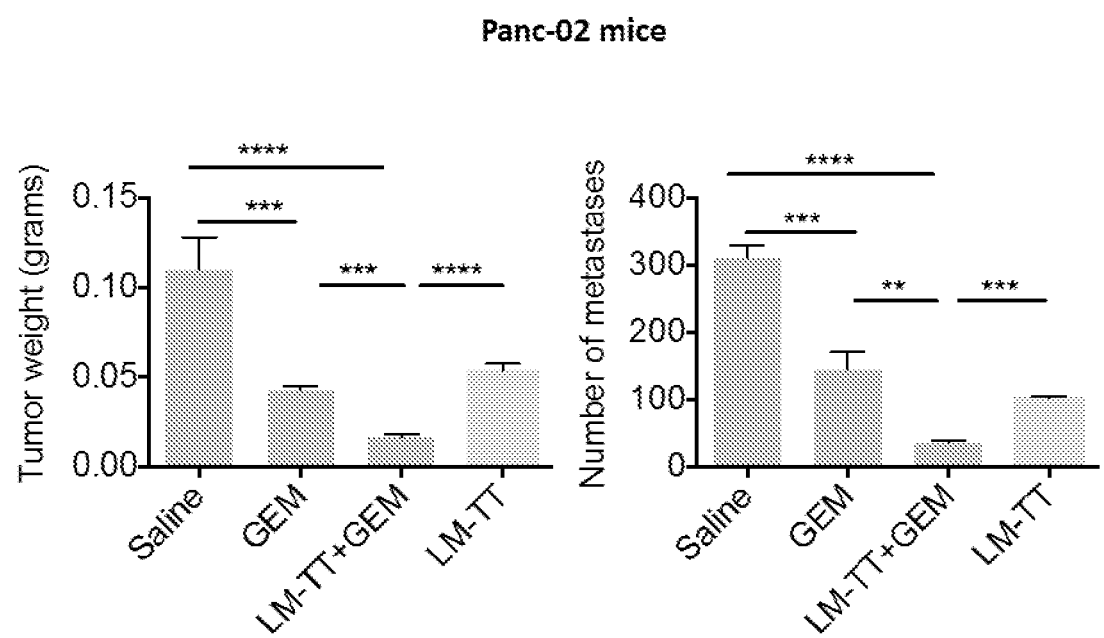
FIG. 6A-6B. GEM and *Listeria*-TT strongly eliminates advanced pancreatic cancer in Panc-02 and KPC mice. (A) Panc-02 model. C57Bl/6 mice were immunized 3 times with the human TT vaccine using 1-week time intervals starting day 0 to generate the memory T cells to TT. Subsequently, Panc-02 tumor cells ($10^5$/100 µl) were injected in mammary fat pad (day 21). When tumors were 10 mm (day 31), one high dose of *Listeria*-TT ($10^7$ CFU) was injected ip, followed (day 36) by daily low doses of *Listeria*-TT ($10^4$ CFU) for 2 weeks (14 doses in total). GEM (1.2 mg/mouse) was administered every three days (5 doses in total) starting on day 34. All mice were euthanized on day 52, and analyzed for the number of metastases (untreated mice have metastases predominantly in the liver and pancreas, and less in mesenchemal lymph nodes and diaphragm). n=5 mice per group. Average of two experiments. Mann-Whitney *p<0.05, p<0.01, *p<0.001, ****p<0.0001. The error bars represent SEM. (B) KPC model. KPC mice of 3.5 months old received the same treatments as the Panc-02 mice. Mice were euthanized when 4.5 months old.

FIG. 6 illustrates the the combination of *Listeria*-TT and Gemcitabine efficacy on advanced pancreatic cancer. Earlier figures show the effect on early pancreatic cancer.

Figure 7A:
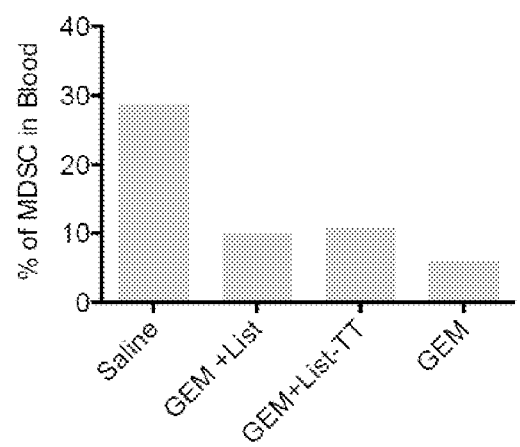
FIG. 7A-7B. (A) GEM reduces the MDSC population in blood of Panc-02 mice. C57B16 mice were challenged with Panc-02 tumor cells and treated with *Listeria*-TT+GEM as described in FIG. 7A. Two days after the last treatment the percentage of MDSC (CD11b+Gr1+) was determined in blood by flow cytometry. N=5 mice per group. Representative of two experiments. (B) GEM reduces the TAM population in metastases of Panc-02 mice. C57B16 mice were challenged with Panc-02 tumor cells and treated with *Listeria*-TT+GEM as described in FIG. 7A. Two days after the last treatment the percentage of TAM (CD11b+F4/80+) was determined in the primary tumors by flow cytometry. N=5 mice per group. Representative of two experiments. The error bars represent SEM.
Figure 7B:
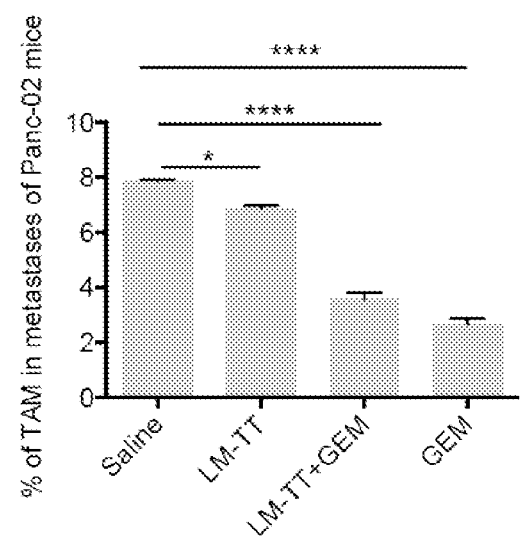

FIG. 7 shows that Gemcitabine reduces the myeloid-derived suppressor cells (MDSC) and tumor-associated macrophage (TAM) populations. Both strongly suppress T cells. By reducing these populations, T cell responses are strongly improved, as shown in Tables 2 and 3.

Table 2 Shows T cell responses in the Panc-02 mice treated with *Listeria*-TT and Gemcitabine. The T cell responses in *Listeria*-TT and Gemcitabine is far better than in the separate groups Table 3 Shows T cell responses in the KPC mice treated with *Listeria*-TT and Gemcitabine. The T cell responses in *Listeria*-TT and Gemcitabine is far better than in the separate groups Table 4 shows that the combination of *Listeria*-TT and Gemcitabine reduces inhibitory cytokines produced by MDSC and TAM, and improve expression levels of CD80 involved in T cell stimulation.

Figure 8:
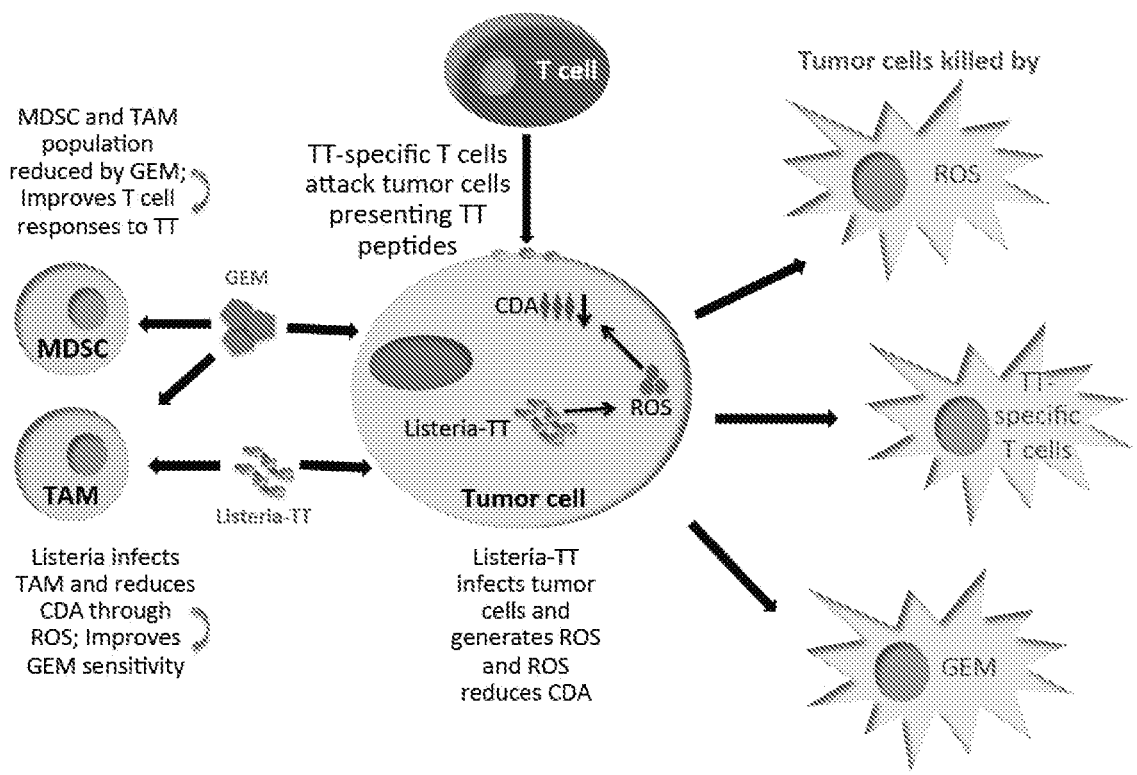
FIG. 8. Synergistic effects of *Listeria*-TT and GEM on pancreatic cancer. *Listeria* delivers TT into tumor cells through infection, resulting in highly immunogenic tumor cells, and reactivates memory T cells to TT through infection of DC (not shown). Simultaneously, *Listeria* induces high levels of ROS in tumor cells and macrophages, which improves GEM sensitivity through reduction of CDA. GEM reduces the MDSC and TAM population, resulting in improved T cell responses. These synergistic effects will lead to tumor cell kill by TT-specific T cells, GEM, and by *Listeria*-induced ROS.
Figure 9:
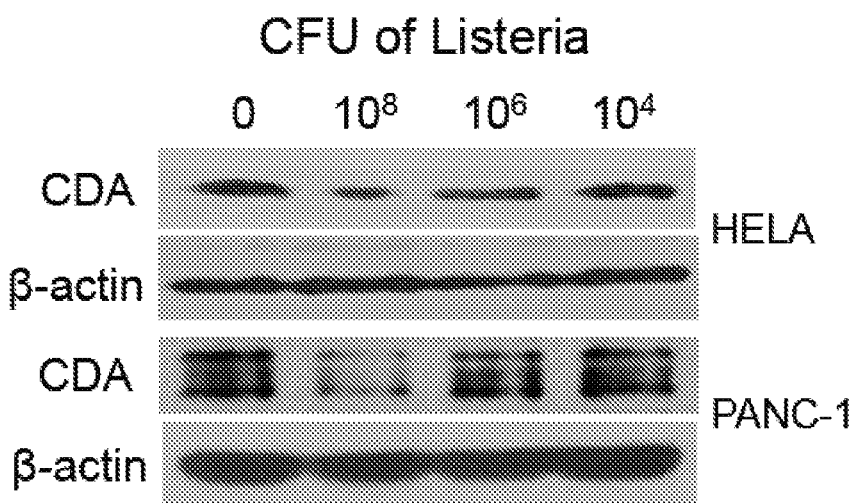
FIG. 9. *Listeria* reduces CDA. Hela cells (human cervical cancer cell line) or PANC-1 (human pancreatic cancer cell line) were cultured for 2 hrs with various numbers of CFU of *Listeria* (LM) ($10^8$, $10^6$, and $10^4$ CFU/ml), and then cultured overnight with Gentamicin to kill all extracellular bacteria. CDA expression was analyzed by western blotting using rabbit anti-human CDA antibodies.
Figure 10:
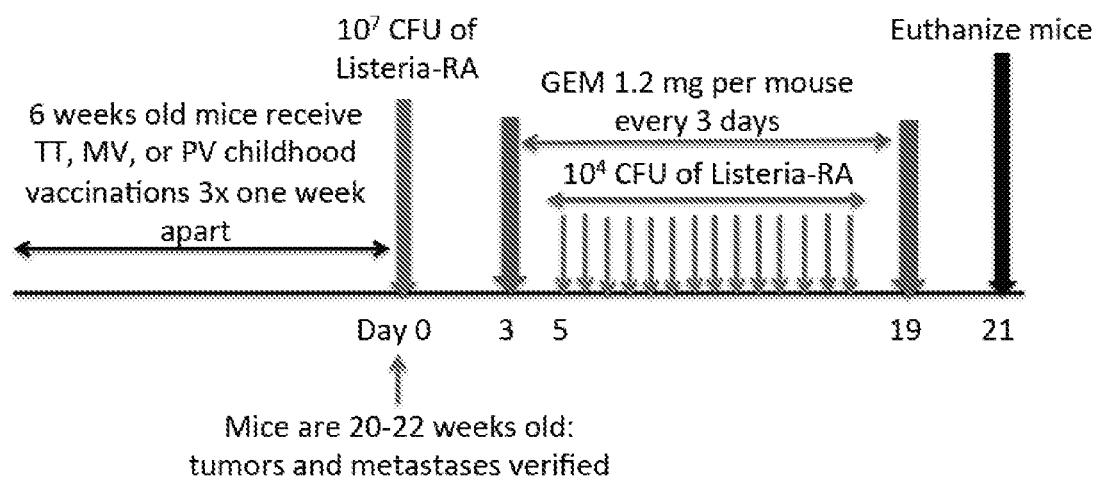
FIG. 10. Schematic view of immunization protocol of *Listeria*-recall antigen and Gemcitabine in mice.

FIG. 8 shows a new model that combines *Listeria*-recall antigens with gemcitabine (GEM). *Listeria* induces high levels of reactive oxygen species (ROS) and ROS reduces the levels of the enzyme cytidine deaminase (CDA). CDA is an enzyme that inactivates gemcitabine and is present at high levels in tumor cells and macrophages in cancer patients and tumor-bearing mice. With the use of *Listeria*, tumor cells now become sensitive to Gemcitabine through *Listeria*-induced ROS. FIG. 9 shows that *Listeria* reduces CDA in Hela and PANC-1 tumor cells. FIG. 10 shows an immunization protocol developed for the combination therapy.

TABLE 1

Immunodominant CD8 epitopes in fragments of recall antigens, MHC haplotype, and corresponding mouse strain.

| Recall Antigen (cloned fragment)$^{ref}$ | Epitopes within the cloned fragments reacting with mouse CD8 T cells | MHC haplotype | Mouse strain/syngeneic tumor cell line | Ref for CD8 epitops |
|---|---|---|---|---|
| TT (856-1313)$^6$ | GYNAPGIPL (1228-1236) (SEQ ID NO: 1) | H2-d | BALB/c/4T | 7 |
| MV (38-351) | LDRLVRLIG (52-59 (SEQ ID NO: 2) | H2-k | AKR/J/BW-Sp3 | 8 |
| MV (38-351) | VESPGQLI (81-88) (SEQ ID NO: 3) | H2-k | AKR/J/BW-Sp3 | 8 |
| PV (42-273) | SNAYSHFYDGFSKVP LKDQS (202-221)* (SEQ ID NO: 4) | H2-d | BALB/c/4T1 | 9 |

The numbers between parentheses represent the position of the amino acid within the antigen.
*CD8 epitope is present within the amino acid sequence.

TABLE 2

CD4 and CD8 T cell responses to Listeria-TT improved by GEM in vivo Panc-02 mice.

| | Percentage | | | |
|---|---|---|---|---|
| | Saline | GEM | LM-TT + GEM | LM-TT |
| CD3CD4CD69 | 15.5 | 14.2 | 28.5 | 14.2 |
| CD3CD8CD69 | 16.7 | 15.5 | 33.2 | 15.5 |
| CD3CD4Perforin | 7.9 | 14.9 | 22.7 | 14.9 |
| CD3CD8Perforin | 2.1 | 4.8 | 6.2 | 4.9 |
| CD3CD4Granzyme B | 4.9 | 4.8 | 9.9 | 5.9 |
| CD3CD8Granzyme B | 1.2 | 1.1 | 2.4 | 1.2 |
| CD3CD4IFNγ | 2.6 | 2.7 | 5.0 | 3.0 |
| CD3CD8IFNγ | 0.5 | 0.4 | 0.9 | 0.4 |

Percentage

Panc-02 mice with advanced pancreatic cancer were treated with one high and multiple low doses of *Listeria*-TT (LM-TT) and GEM as described in FIG. 7A. T cells were analyzed in the spleens (of 3 mice pooled) by flow cytometry. This experiment was performed once.

TABLE 3

CD4 and CD8 T cell responses to Listeria-TT improved by GEM in vivo KPC mice.

| | Percentage | | | |
|---|---|---|---|---|
| | Saline | GEM | LM-TT + GEM | LM-TT |
| CD3CD4CD69 | 13.5 | 10.01 | 17.34 | 6.59 |
| CD3CD8CD69 | 12.3 | 17.5 | 23.92 | 18.8 |
| CD3CD4Perforin | 0.26 | 7.90 | 14.27 | 8.22 |
| CD3CD8Perforin | 0.25 | 15.60 | 16.70 | 14.73 |
| CD3CD4Granzyme B | 3.1 | 3.5 | 12.17 | 4.82 |
| CD3CD8Granzyme B | 1.6 | 9.71 | 12.60 | 9.82 |
| CD3CD4IFNγ | 0.3 | 0.0 | 0.16 | 0.41 |
| CD3CD8IFNγ | 0.0 | 1.7 | 3.33 | 1.85 |

KPC mice with advanced pancreatic cancer were treated with one high and multiple low doses of *Listeria*-TT (LM-TT) and GEM as described in FIG. 7A. T cells were analyzed in the spleen by flow cytometry. This experiment was performed once.

TABLE 4

Analysis of MDSC and TAM in Panc-02 mice.

| | Treatment | | | |
|---|---|---|---|---|
| | Saline | LM-TT | LM-TT + GEM | GEM |
| Percentage of MDSC (CD11b+Gr1+) in Blood | | | | |
| IL-10 | 3.46 | 2.44 | 1.45 | 2.76 |
| IL-6 | 4.25 | 4.05 | 2.70 | 3.59 |
| TNFα | 3.64 | 8.42 | 11.6 | 8.49 |
| MARCO | 3.38 | 3.70 | 1.79 | 3.84 |
| CD80 | 1.28 | 1.08 | 1.17 | 1.78 |
| Percentage of TAM (CD11b+F4/80+) in Metastases | | | | |
| IL-10 | 1.45 | 0.65 | 0.72 | 1.47 |
| IL-6 | 1.09 | 0.76 | 0.42 | 1.25 |
| TNFα | 4.78 | 8.73 | 8.04 | 8.85 |
| MARCO | 1.96 | 2.16 | 1.33 | 1.94 |
| CD80 | 1.93 | 3.07 | 5.26 | 4.28 |

Panc-02 mice with advanced pancreatic cancer were treated with one high and multiple low doses of *Listeria*-TT (LM-TT) and GEM as described in FIG. 7A. MDSC and TAM were analyzed in the metastases by flow cytometry. Metastases of 3 mice were pooled. This experiment was performed once.

Discussion

The success of cancer immunotherapy has been hindered by two major problems. One problem is that tumor-associated antigens (TAA), used in cancer vaccines, are often self-antigens that are overexpressed or mutated in tumor cells compared to normal cells. The T cells in the thymus have been taught earlier in life not to react to self-antigens, and therefore it is difficult to induce strong T cell responses to TAA. The other problem is that most cancer patients are old, and the elderly react less efficiently to vaccines than young adults. This is often due to lack of naïve T cells (only generated at young age, and are used during life) that react for the first time to a new antigen and are responsible for the generation of memory T cells upon repeated exposures with the same antigen. None of the vaccines currently available avoids the need of naïve T cells at an older age, and none of the vaccines allow delivery of highly immunogenic recall antigens directly into tumor cells by live attenuated bacteria.

The present approach overcomes the problem of poorly immunogenic antigens in cancer vaccination by using highly immunogenic recall antigens, and at the same time avoids the need of naïve T cells in older age. The present procedure involves reactivating memory T cells to foreign highly immunogenic antigens to which most individuals have been exposed during childhood when plenty of naïve T cells are available, such as tetanus toxoid (TT), measle virus (MV), polio virus (PV) antigens, and by the selective delivery of these antigens into tumor cells by an attenuated non-toxic and non-pathogenic bacterium, such as *Listeria monocytogenes*. These memory T cells will now kill infected tumor cells presenting the highly immunogenic antigens. In previous studies, *Listeria* has been used for the selective delivery of anticancer agents to the tumor microenvironment and into tumor cells of metastases and tumors. *Listeria* was effectively cleared by the immune system in normal tissue but not in the heavily immune-suppressed microenvironment of metastasis and primary tumor (10, 11).

However, immune suppression may not be completely overcome by this treatment. This problem can be resolved by combining the *Listeria*-recall antigens with a chemotherapeutic, such as gemcitabine, that reduces the number of myeloid-derived suppressor cells (MDSCs). MDSCs are the most important contributor to immune suppression in the tumor microenvironment.

All together, these results are very impressive. Also, the mechanism that *Listeria*-induced ROS improves gemcitabine sensitivity is very important because most clinicians don't want to stop gemcitabine treatment in pancreatic cancer patients. And most important, the combination therapy is effective against advanced pancreatic cancer, and can work at young and old age, because elderly patients lack naïve T cells (required to develop memory T cells). With the present approach, one immediately reactivates memory T cells to tetanus toxoid antigens, measle virus antigens and poliovirus antigens, and avoids the need of naïve T cells at older age. Since the *Listeria* with the recall antigens selectively infect tumor cells in vivo, the memory T cells that circulate in blood for life can now kill the infected tumor cells. These memory T cells were generated during childhood with the childhood vaccines.

The most obvious uses of the present invention are treatment of types of cancer for which there are practically no effective treatments, such as pancreatic cancer, which is almost always detected in metastatic form, or ovarian cancer. Good candidates also include cancers for which surgery to remove the primary tumor is often not an option because of tumor location, such as head and neck cancers or inoperable hepatocellular carcinoma. A third cohort of patients that would be expected to benefit from such therapy are patients with various types of metastatic disease, which is recurrent or refractory to standard treatments, such as for example lung and colon cancers as well as breast cancer.

REFERENCES

1. Achkar J M, Fries B C. 2010. *Candida* infections of the genitourinary tract. *Clinical microbiology reviews* 23: 253-73.
2. Eroles P, Sentandreu M, Elorza M V, Sentandreu R. 1997. The highly immunogenic enolase and Hsp70p are adventitious *Candida albicans* cell wall proteins. *Microbiology* 143 (Pt 2): 313-20.
3. Lechner M G, Epstein A L. 2011. A new mechanism for blocking myeloid-derived suppressor cells by CpG. *Clini-* cal cancer research: an official journal of the American Association for Cancer Research 17: 1645-8.
4. Bracci L, Schiavoni G, Sistigu A, Belardelli F. 2014. Immune-based mechanisms of cytotoxic chemotherapy: implications for the design of novel and rationale-based combined treatments against cancer. *Cell Death Differ* 21: 15-25.
5. Rice J, Buchan S, Stevenson F K. 2002. Critical components of a DNA fusion vaccine able to induce protective cytotoxic T cells against a single epitope of a tumor antigen. *Journal of immunology* 169: 3908-13.
6. Reveneau N, Geoffroy M C, Locht C, Chagnaud P, Mercenier A. 2002. Comparison of the immune responses induced by local immunizations with recombinant *Lactobacillus plantarum* producing tetanus toxin fragment C in different cellular locations. *Vaccine* 20: 1769-77.
7. Weidinger G, Czub S, Neumeister C, Harriott P, ter Meulen V, Niewiesk S. 2000. Role of CD4(+) and CD8(+) T cells in the prevention of measles virus-induced encephalitis in mice. *J Gen Virol* 81: 2707-13.
8. Usherwood E J, Nash A A. 1995. Lymphocyte recognition of picornaviruses. *J Gen Virol* 76 (Pt 3): 499-508.
9. Chandra D, Jahangir A, Quispe-Tintaya W, Einstein M H, Gravekamp C. 2013. Myeloid-derived suppressor cells have a central role in attenuated *Listeria monocytogenes*-based immunotherapy against metastatic breast cancer in young and old mice. *British Journal of Cancer* 108: 2281-2290. Epub 2013 May 2.
10. Quispe-Tintaya W, Chandra D, Jahangir A, Harris M, Casadevall A, Dadachova E, Gravekamp C. 2013. Non-toxic radioactive *Listeria*(at) is a highly effective therapy against metastatic pancreatic cancer. *Proc Natl Acad Sci USA.* 21; 110(21):8668-73, Epub 2013 Apr. 22.
11. U.S. Patent Application Publication No. 2014/0147379 A1, published May 29, 2014, Dadachova et al., Radio-bacteria for Therapy of Cancer.
12. Kim, S. H., Castro, F., Paterson, Y. & Gravekamp, C. 2009. High efficacy of a *Listeria*-based vaccine against metastatic breast cancer reveals a dual mode of action. *Cancer Res* 69, 5860-5866.

What is claimed is:

1. An arrangement, in a tumor microenvironment in a subject, of a cancer immunotherapy compound and a chemotherapeutic compound, the cancer immunotherapy compound having exited a first myeloid-derived suppressor cell in the tumor microenvironment and entering a tumor cell in the tumor microenvironment, the chemotherapeutic compound causing cell death in a second myeloid-derived suppressor cell in the tumor microenvironment, the cancer immunotherapy compound comprising:

an attenuated bacteria configured to induce an immune response in the subject to the tumor cell substantially at least equal in magnitude to an immune response in the subject to a pathogen recognized by the immune system of the subject, the attenuated bacteria configuration including having as a payload a fusion of a truncated non-cytolytic Listeriolysin-O and a non-self external antigen of the pathogen, the payload lacking a cancer specific antigen, the Listeriolysin-O including a signal sequence for inducing the tumor cell to present the non-self external antigen on an external surface of the tumor cell, wherein an intraperitoneal injection of the cancer immunotherapy compound into the subject permits survival of the cancer immunotherapy compound until the attenuated bacteria infects the first myeloid-derived suppressor cell, travel of the first myeloid-derived suppressor cell to the tumor microenvironment, and subsequent exit, facilitated by the Listeriolysin-O, of the cancer immunotherapy compound from the first myeloid-derived suppressor cell, delivers the cancer immunotherapy compound to the tumor microenvironment, infection of the tumor cell by the cancer immunotherapy compound, facilitated by immune suppression in the tumor microenvironment caused at least in part by the second myeloid-derived suppressor cell prior to the cell death, and subsequent secretion by the cancer immunotherapy compound of the payload in the tumor cell causes the tumor cell, in response to the signal sequence, to present the non-self external antigen on the external surface of the tumor cell, recognition of the non-self external antigen by the immune system causes the immune response to the tumor cell, and the immune response is enhanced by a reduction of immune suppression in the tumor microenvironment caused by the cell death caused by the chemotherapeutic compound.

2. The arrangement of claim 1, wherein the attenuated bacteria is an attenuated strain of one or more of *Listeria monocytogenes, Salmonella thyphimurium, Vibrio cholera, Clostridium*, and *Bifidobacterium breve*.

3. The arrangement of claim 1, wherein the non-self external antigen is an epitope of one or more of tetanus toxoid, measle virus, and polio virus.

4. The arrangement of claim 1, wherein the chemotherapeutic compound is gemcitabine.

5. The arrangement of claim 1, wherein the subject is a target subject and the arrangement includes, with regard to $10^4$ CFU of the cancer immunotherapy compound and 1.2 mg of the chemotherapeutic compound being clinically effective for a mouse subject, the corresponding clinically effective respective amounts of the cancer immunotherapy compound and the chemotherapeutic compound for the target subject.

* * * * *

SEQUENCE LISTING

<160> NUMBER OF SEQ ID NOS: 10

<210> SEQ ID NO 1
<211> LENGTH: 9
<212> TYPE: PRT
<213> ORGANISM: Artificial Sequence
<220> FEATURE:
<223> OTHER INFORMATION: tetanus toxid

<400> SEQUENCE: 1

Gly Tyr Asn Ala Pro Gly Ile Pro Leu
1               5

<210> SEQ ID NO 2
<211> LENGTH: 9
<212> TYPE: PRT
<213> ORGANISM: Artificial Sequence
<220> FEATURE:
<223> OTHER INFORMATION: measle virus

<400> SEQUENCE: 2

Leu Asp Arg Leu Val Arg Leu Ile Gly
1               5

<210> SEQ ID NO 3
<211> LENGTH: 8
<212> TYPE: PRT
<213> ORGANISM: Artificial Sequence
<220> FEATURE:
<223> OTHER INFORMATION: measle virus

<400> SEQUENCE: 3

Val Glu Ser Pro Gly Gln Leu Ile
1               5

<210> SEQ ID NO 4
<211> LENGTH: 20
<212> TYPE: PRT
<213> ORGANISM: polio virus

<400> SEQUENCE: 4

Ser Asn Ala Tyr Ser His Phe Tyr Asp Gly Phe Ser Lys Val Pro Leu
1               5                   10                  15

Lys Asp Gln Ser
            20

```
<210> SEQ ID NO 5
<211> LENGTH: 458
<212> TYPE: PRT
<213> ORGANISM: Artificial Sequence
<220> FEATURE:
<223> OTHER INFORMATION: tetanus toxid

<400> SEQUENCE: 5

Ser Thr Pro Ile Pro Phe Ser Tyr Ser Lys Asn Leu Asp Cys Trp Val
1               5                   10                  15

Asp Asn Glu Glu Asp Ile Asp Val Ile Leu Lys Lys Ser Thr Ile Leu
            20                  25                  30

Asn Leu Asp Ile Asn Asn Asp Ile Ile Ser Asp Ile Ser Gly Phe Asn
        35                  40                  45

Ser Ser Val Ile Thr Tyr Pro Asp Ala Gln Leu Val Pro Gly Ile Asn
    50                  55                  60

Gly Lys Ala Ile His Leu Val Asn Asn Glu Ser Ser Glu Val Ile Val
65                  70                  75                  80

His Lys Ala Met Asp Ile Glu Tyr Asn Asp Met Phe Asn Asn Phe Thr
                85                  90                  95

Val Ser Phe Trp Leu Arg Val Pro Lys Val Ser Ala Ser His Leu Glu
            100                 105                 110

Gln Tyr Gly Thr Asn Glu Tyr Ser Ile Ile Ser Ser Met Lys Lys His
        115                 120                 125

Ser Leu Ser Ile Gly Ser Gly Trp Ser Val Ser Leu Lys Gly Asn Asn
    130                 135                 140

Leu Ile Trp Thr Leu Lys Asp Ser Ala Gly Glu Val Arg Gln Ile Thr
145                 150                 155                 160

Phe Arg Asp Leu Pro Asp Lys Phe Asn Ala Tyr Leu Ala Asn Lys Trp
                165                 170                 175

Val Phe Ile Thr Ile Thr Asn Asp Arg Leu Ser Ser Ala Asn Leu Tyr
            180                 185                 190

Ile Asn Gly Val Leu Met Gly Ser Ala Glu Ile Thr Gly Leu Gly Ala
        195                 200                 205

Ile Arg Glu Asp Asn Asn Ile Thr Leu Lys Leu Asp Arg Cys Asn Asn
    210                 215                 220

Asn Asn Gln Tyr Val Ser Ile Asp Lys Phe Arg Ile Phe Cys Lys Ala
225                 230                 235                 240

Leu Asn Pro Lys Glu Ile Glu Lys Leu Tyr Thr Ser Tyr Leu Ser Ile
                245                 250                 255

Thr Phe Leu Arg Asp Phe Trp Gly Asn Pro Leu Arg Tyr Asp Thr Glu
            260                 265                 270

Tyr Tyr Leu Ile Pro Val Ala Ser Ser Ser Lys Asp Val Gln Leu Lys
        275                 280                 285

Asn Ile Thr Asp Tyr Met Tyr Leu Thr Asn Ala Pro Ser Tyr Thr Asn
    290                 295                 300

Gly Lys Leu Asn Ile Tyr Tyr Arg Arg Leu Tyr Asn Gly Leu Lys Phe
305                 310                 315                 320

Ile Ile Lys Arg Tyr Thr Pro Asn Asn Glu Ile Asp Ser Phe Val Lys
                325                 330                 335

Ser Gly Asp Phe Ile Lys Leu Tyr Val Ser Tyr Asn Asn Asn Glu His
            340                 345                 350

Ile Val Gly Tyr Pro Lys Asp Gly Asn Ala Phe Asn Asn Leu Asp Arg
        355                 360                 365
```

```
Ile Leu Arg Val Gly Tyr Asn Ala Pro Gly Ile Pro Leu Tyr Lys Lys
    370                 375                 380

Met Glu Ala Val Lys Leu Arg Asp Leu Lys Thr Tyr Ser Val Gln Leu
385                 390                 395                 400

Lys Leu Tyr Asp Asp Lys Asn Ala Ser Leu Gly Leu Val Gly Thr His
                405                 410                 415

Asn Gly Gln Ile Gly Asn Asp Pro Asn Arg Asp Ile Leu Ile Ala Ser
                420                 425                 430

Asn Trp Tyr Phe Asn His Leu Lys Asp Lys Ile Leu Gly Cys Asp Trp
                435                 440                 445

Tyr Phe Val Pro Thr Asp Glu Gly Trp Thr
                450                 455
```

<210> SEQ ID NO 6
<211> LENGTH: 1374
<212> TYPE: DNA
<213> ORGANISM: Artificial Sequence
<220> FEATURE:
<223> OTHER INFORMATION: tetanus toxid

<400> SEQUENCE: 6

```
tcaacaccaa ttccattttc ttattctaaa aatctggatt gttgggttga taatgaagaa      60
gatatagatg ttatattaaa aaagagtaca atttttaaatt tagatattaa taatgatatt    120
atatcagata tatctgggtt taattcatct gtaataacat atccagatgc tcaattggtg    180
cccggaataa atggcaaagc aatacattta gtaaacaatg aatcttctga agttatagtg    240
cataaagcta tggatattga atataatgat atgtttaata attttaccgt tagctttttgg   300
ttgagggttc ctaaagtatc tgctagtcat ttagaacaat atggcacaaa tgagtattca    360
ataattagct ctatgaaaaa acatagtcta tcaataggat ctggttggag tgtatcactt    420
aaaggtaata acttaatatg gactttaaaa gattccgcgg gagaagttag acaaataact    480
tttagggatt tacctgataa atttaatgct tatttagcaa ataaatgggt ttttataact    540
attactaatg atagattatc ttctgctaat ttgtatataa atggagtact tatgggaagt    600
gcagaaatta ctggttttagg agctattaga aggataataa ataataactatt aaaactagat    660
agatgtaata ataataatca atacgtttct attgataaat ttaggatatt ttgcaaagca    720
ttaaatccaa aagagattga aaaattatac acaagttatt tatctataac cttttttaaga   780
gacttctggg gaaaccctttt acgatatgat acagaatatt atttaatacc agtagcttct    840
agttctaaag atgttcaatt gaaaaatata acagattata tgtatttgac aaatgcgcca    900
tcgtatacta acggaaaatt gaatatatat tatagaaggt tatataatgg actaaaattt    960
attataaaaa gatatacacc taataatgaa atagattctt tgttaaaatc aggtgatttt   1020
attaaattat atgtatcata taacaataat gagcacattg taggttatcc gaaagatgga   1080
aatgccttta ataatcttga tagaattcta agagtaggtt ataatgcccc aggtatccct   1140
ctttataaaa aaatggaagc agtaaaattg cgtgatttaa aaacctattc tgtacaactt   1200
aaattatatg atgataaaaa tgcatcttta ggactagtag gtacccataa tggtcaaata   1260
ggcaacgatc caaataggga tatattaatt gcaagcaact ggtactttaa tcatttaaaa   1320
gataaaatttt taggatgtga ttggtacttt gtacctacag atgaaggatg gaca         1374
```

<210> SEQ ID NO 7
<211> LENGTH: 224
<212> TYPE: PRT
<213> ORGANISM: polio virus

<400> SEQUENCE: 7

```
Arg Ser Arg Ser Glu Ser Ser Ile Glu Ser Phe Phe Ala Arg Gly Ala
1               5                   10                  15

Cys Val Thr Ile Met Thr Val Asp Asn Pro Ala Ser Thr Thr Asn Lys
            20                  25                  30

Asp Lys Leu Phe Ala Val Trp Lys Ile Thr Tyr Lys Asp Thr Val Gln
        35                  40                  45

Leu Arg Arg Lys Leu Glu Phe Phe Thr Tyr Ser Arg Phe Asp Met Glu
    50                  55                  60

Leu Thr Phe Val Val Thr Ala Asn Phe Thr Glu Thr Asn Asn Gly His
65                  70                  75                  80

Ala Leu Asn Gln Val Tyr Gln Ile Met Tyr Val Pro Pro Gly Ala Pro
                85                  90                  95

Val Pro Glu Lys Trp Asp Asp Tyr Thr Trp Gln Thr Ser Ser Asn Pro
            100                 105                 110

Ser Ile Phe Tyr Thr Tyr Gly Thr Ala Pro Ala Arg Ile Ser Val Pro
        115                 120                 125

Tyr Val Gly Ile Ser Asn Ala Tyr Ser His Phe Tyr Asp Gly Phe Ser
    130                 135                 140

Lys Val Pro Leu Lys Asp Gln Ser Ala Ala Leu Gly Asp Ser Leu Tyr
145                 150                 155                 160

Gly Ala Ala Ser Leu Asn Asp Phe Gly Ile Leu Ala Val Arg Val Val
                165                 170                 175

Asn Asp His Asn Pro Thr Lys Val Thr Ser Lys Ile Arg Val Tyr Leu
            180                 185                 190

Lys Pro Lys His Ile Arg Val Trp Cys Pro Arg Pro Pro Arg Ala Val
        195                 200                 205

Ala Tyr Tyr Gly Pro Gly Val Asp Tyr Lys Asp Gly Thr Leu Thr Pro
    210                 215                 220
```

<210> SEQ ID NO 8
<211> LENGTH: 672
<212> TYPE: DNA
<213> ORGANISM: polio virus

<400> SEQUENCE: 8

```
aggtcaaggt cagagtctag catagagtct ttcttcgcgc ggggtgcatg cgtgaccatt     60
atgaccgtgg ataacccagc ttccaccacg aataaggata agctatttgc agtgtggaag    120
atcacttata aagatactgt ccagttacgg aggaaattgg agttcttcac ctattctaga    180
tttgatatgg aacttacctt tgtggttact gcaaatttca ctgagactaa caatgggcat    240
gccttaaatc aagtgtacca aattatgtac gtaccaccag gcgctccagt gcccgagaaa    300
tgggacgact acacatggca aacctcatca aatccatcaa tcttttacac ctacggaaca    360
gctccagccc ggatctcggt accgtatgtt ggtatttcga acgcctattc acacttttac    420
gacggttttt ccaaagtacc actgaaggac cagtcggcag cactaggtga ctccctttat    480
ggtgcagcat ctctaaatga cttcggtatt ttggctgtta gagtagtcaa tgatcacaac    540
ccgaccaagg tcacctccaa aatcagagtg tatctaaaac ccaaacacat cagagtctgg    600
tgcccgcgtc caccgagggc agtggcgtac tacggccctg gagtggatta caaggatggt    660
acgcttacac cc                                                        672
```

```
<210> SEQ ID NO 9
<211> LENGTH: 157
<212> TYPE: PRT
<213> ORGANISM: Artificial Sequence
<220> FEATURE:
<223> OTHER INFORMATION: measle virus

<400> SEQUENCE: 9

Pro Ile Pro Gly Asp Ser Ser Ile Thr Thr Arg Ser Arg Leu Leu Asp
1               5                   10                  15

Arg Leu Val Arg Leu Ile Gly Asn Pro Asp Val Ser Gly Pro Lys Leu
            20                  25                  30

Thr Gly Ala Leu Ile Gly Ile Leu Ser Leu Phe Val Glu Ser Pro Gly
        35                  40                  45

Gln Leu Ile Gln Arg Ile Thr Asp Asp Pro Asp Val Ser Ile Arg Leu
    50                  55                  60

Leu Glu Val Val Gln Ser Asp Gln Ser Gln Ser Gly Leu Thr Phe Ala
65                  70                  75                  80

Ser Arg Gly Thr Asn Met Glu Asp Glu Ala Asn Gln Tyr Phe Ser His
                85                  90                  95

Asp Asp Pro Ile Ser Ser Asp Gln Ser Arg Phe Gly Trp Phe Glu Asn
            100                 105                 110

Lys Glu Ile Ser Asp Ile Glu Val Gln Asp Pro Glu Gly Phe Asn Met
        115                 120                 125

Ile Leu Gly Thr Ile Leu Ala Gln Ile Trp Ala Leu Leu Ala Lys Ala
    130                 135                 140

Val Thr Ala Pro Asp Thr Ala Ala Asp Ser Glu Leu Arg
145                 150                 155

<210> SEQ ID NO 10
<211> LENGTH: 471
<212> TYPE: DNA
<213> ORGANISM: Artificial Sequence
<220> FEATURE:
<223> OTHER INFORMATION: measle virus

<400> SEQUENCE: 10
ccaatccctg gagattcctc aattaccact cgatccagac ttctggaccg gttggtcagg     60
ttaattggaa acccggatgt gagcgggccc aaactaacag gggcactaat aggtatatta    120
tccttatttg tggagtctcc aggtcaattg attcagagga tcaccgatga ccctgacgtt    180
agcataaggc tgttagaggt tgtccagagt gaccagtcac aatctggcct taccttcgca    240
tcaagaggta ccaacatgga ggatgaggcg aaccaatact tttcacatga tgatccaatt    300
agtagtgatc aatccaggtt cggatggttc gagaacaagg aaatctcaga tattgaagtg    360
caagaccctg agggattcaa catgattctg ggtaccatcc tagcccaaat ttgggccttg    420
ctcgcaaagg cggttacggc cccagacacg gcagctgatt cggagctaag a             471
```